US008025395B2

(12) United States Patent
    Quintana

(10) Patent No.: US 8,025,395 B2
(45) Date of Patent: Sep. 27, 2011

(54) INDUSTRIAL SAFETY GOGGLES WITH FRAME FOR OPHTHALMIC MICAS AND IMPACT PROTECTION MICA

(76) Inventor: Alejandro Arturo Goebel Quintana, Naucalpan de Juarez (MX)

( * ) Notice: Subject to any disclaimer, the term of this patent is extended or adjusted under 35 U.S.C. 154(b) by 0 days.

(21) Appl. No.: 12/523,978

(22) PCT Filed: Feb. 27, 2008

(86) PCT No.: PCT/MX2008/000031
    § 371 (c)(1),
    (2), (4) Date: Jul. 21, 2009

(87) PCT Pub. No.: WO2008/105648
    PCT Pub. Date: Sep. 4, 2008

(65) Prior Publication Data
    US 2010/0118258 A1        May 13, 2010

(30) Foreign Application Priority Data

Feb. 27, 2007  (MX) ................... MX/U/2007/000075

(51) Int. Cl.
    *G02C 1/00*  (2006.01)
(52) U.S. Cl. .............. 351/86; 351/41; 351/62; 351/154; 2/436
(58) Field of Classification Search ............... 351/41, 351/44, 47, 48, 57, 58, 62, 83–86, 122, 123, 351/154, 156–158; 2/426–437, 452
    See application file for complete search history.

(56) References Cited

U.S. PATENT DOCUMENTS

| 1,925,588 | A | * | 9/1933 | Gagnon ............................ 2/441 |
| 4,240,718 | A | * | 12/1980 | Wichers ......................... 351/62 |
| 4,952,043 | A |   | 8/1990 | Werner et al. |
| 5,321,443 | A |   | 6/1994 | Huber et al. |
| 6,149,268 | A | * | 11/2000 | Hall et al. ....................... 351/62 |
| 2004/0117898 | A1 | | 6/2004 | Penque et al. |

FOREIGN PATENT DOCUMENTS

| GB | 2224134 | 4/1990 |
| WO | 79/00548 | 8/1979 |
| WO | 2005/092262 | 10/2005 |

* cited by examiner

*Primary Examiner* — Huy K Mai
(74) *Attorney, Agent, or Firm* — Vedder Price P.C.

(57) ABSTRACT

The invention relates to industrial safety goggles provided with permanent ophthalmic micas having a full impact protection mica positioned thereon, wherein said impact protection mica is made from polycarbonate, provides protection against ultraviolet rays and can be removed, thereby enabling the frames to be used as ophthalmic glasses. Said goggles include a ventilation area and the ophthalmic micas have an improved visual field owing to the design of the frame to which they are mounted and fixed using angular incisions in the frame. The frame is provided with an open space at both eyes between the mica and the end of the rim, which provides ventilation and prevents the fogging of the graduated micas. The sidepieces of the goggles are designed to curve at the ends thereof, so that the goggles can be put in place without the user having to remove his/her industrial safety helmet. In addition, said sidepieces are provided with removable pad which are press-fitted and which are joined by a cord that enables the goggles to be hung around the neck when not in use. Said cord takes the form of a resistance cord that can break should the goggles be impeded by any object that could cause an accident.

7 Claims, 7 Drawing Sheets

FIG. 3a
FIG. 3b
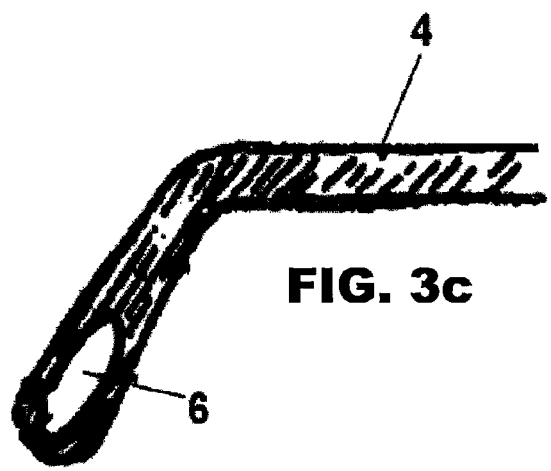
FIG. 3c

INDUSTRIAL SAFETY GOGGLES WITH FRAME FOR OPHTHALMIC MICAS AND IMPACT PROTECTION MICA

TECHNICAL FIELD

The instant invention relates to industrial safety goggles and particularly to goggles including an impact protection mica and graduated micas on the same frame.

BACKGROUND OF THE INVENTION

In the field of industrial safety and personal protection equipments, several products have been developed that fulfill basically the purpose of protecting the user against the several classes of risks occurring in the industries and activities endangering the corporal integrity of the user.

Thus, with regard to eye protection, there are equipments such as industrial safety goggles consisting, generally speaking, of an assembly including a protection lens and a support frame, with a rim portion defining a window to receive the protection lens. The main function of said goggles is to protect against dust or elements that can impact against the eyes when a given work is performed.

On the other hand, in the state of the art, there exist devices used to place a removable cover top protect against sun beams on the conventional frame of prescription or graduated lenses, such as illustrated in documents U.S. Pat. No. 5,321,443 and U.S. Pat. No. 4,952,043. With the above device a person requiring graduated lenses can perform his/her activities and also count on the presence of an eye protection element.

Moreover, there exist inserts with a front frame including graduated lenses but without sidepieces, in such a way that the insert can be placed on a special frame permitting the placement of a protection cover for the graduated lenses and thus for the user's eyes, both against sun beams as well as against small objects that could impact against said cover.

Specifically, an attempt to combine ophthalmic or prescription lenses with an impact protection in the goggles without inserts is shown in document WO2005/092262, in which goggles including a first region comprising a primary sight area located in the front part of the goggles and a second region comprising a peripheral sight area surrounding the primary sight area, including optical correction lenses.

SUMMARY OF THE INVENTION

Thus, one object of the instant invention is to offer goggles integrating the fulfillment of the ophthalmic needs of the user with the protection and safety needs requested by his/her labor activity, and all this on one single frame.

The invention provides an industrial safety goggles with permanent ophthalmic micas having a full impact protection mica positioned thereon, wherein said impact protection mica is made from polycarbonate, provides protection against ultraviolet rays and can be removed, thereby enabling the frames to be used as ophthalmic glasses. Said goggles include a ventilation area and the ophthalmic micas have an improved visual field owing to the design of the frame to which they are mounted and fixed using angular incisions in the frame. The frame is provided with an open space at both eyes between the mica and the end of the rim, which provides ventilation and prevents the fogging of the graduated micas. The sidepieces of the goggles are designed to curve at the ends thereof, so that the goggles can be put in place without the user having to remove his/her industrial safety helmet. In addition, said sidepieces are provided with removable pad which are press-fitted and which are joined by a cord that enables the goggles to be hung around the neck when not in use. Said cord takes the form of a resistance cord that can break should the goggles be impeded by any object that could cause an accident.

The goggles proposed by the inventor include a frame containing ophthalmic or graduated micas and permitting the use of larger micas in order to improve the user's visual field; even in the case of bifocal micas in which the visual field has to be larger in order to improve the reading area, this is obtained through the mounting system permitting the mica to extend up to the frame bridge. The outer part of the ophthalmic mica is free from peripheral obstruction permitting a wider panoramic vision due to the angular mounting system of the ophthalmic mica.

Because of it design, the frame can even be used only as ophthalmic goggles if the impact protection mica is removed.

Because of its design, the frame allows ventilation and prevents the falling of the ophthalmic or graduated micas, ensuring a firm mounting and preventing the rotation and/or accidental disassembly of the ophthalmic or graduated micas from the frame.

Moreover, the goggles sidepieces have an oval hole at their ends to which a pad is placed, attached to a cord to which another pad is attached at its other end that is also placed in the hole of the other sidepiece integrating the frame. The pads are removable, soft and anti-slippage and offer better comfort in the mastoid area and ensure that the frame does not slip.

Each sidepiece fulfills several functions: the first one being that the pads are placed on them to allow a better adherence of the goggles onto the user's head; the second function being that said pads are joined through a cord that allows the goggles to hang from the neck of the user when the industrial protection goggles are not in use, with the advantage that the cord can break easily if a sudden intense tension occurs in case the goggles get accidentally blocked by any object, preventing thus an accident.

Additionally, the curvature of the end of each sidepiece allows the user to put on the goggles without the need to remove the safety helmet.

The frame is in the shape of a complete ring offering a better resistance against impact and prolonging the useful life of the industrial protection goggles.

The impact protection mica made of polycarbonate has integrated tabs in the sides that are inserted in the grooves of the frame to ensure a firm fastening.

The center of the impact protection mica has a fastening system onto the protection mica that fits into its counterpart forming an integral part of the frame in order to ensure a firm fastening.

The ophthalmic lenses mounting system and the frame are one single unit. There is no need for additional loose pieces preventing thus accessory losses.

A universal-type frame bridge is used having an inserted soft and anti-slippage pad offering a convenient adjustment on the nose bridge.

The pads have an integrated cord to hang around the neck when the safety goggles are not being used.

The universal size sidepieces have the curvature of the skull for a convenient adjustment and offer better safety against impacts given their width at the point of union with the front part.

The frame includes an upper protection and side protections to protect the eyes against projectiles or impacts.

The sidepieces have additional lateral protections continuing the front part of the frame, fitting because of their extended design, providing a better protection.

The mounting system of the ophthalmic micas is innovative because the frame has a channel and an open space in both eyes between the mica and the end of the ring permitting ventilation and preventing fogging of the graduated ophthalmic micas, ensuring a firm assembly and preventing the rotation and/or accidental disassembly of the ophthalmic micas from the frame.

Each ring includes an angular notch that can take the form of either an angular cut or projection permitting the firm attachment of the ophthalmic mica. Said angular cut or projection is a continuation of the bevel or channel serving to mount the mica on the frame, ensuring a firm assembly and preventing the rotation and/or accidental disassembly of the ophthalmic micas.

Upon disassembling the polycarbonate impact protection mica, the goggles can be used as daily use graduation lens.

BRIEF DESCRIPTION OF THE DRAWINGS

In order to offer a better understanding of the invention, said invention will be described hereinafter together with the attached drawings in which:

FIGS. 3a, 3b and 3c show in a detailed way the pad of the sidepieces of the goggles of FIG. 1;

DETAILED DESCRIPTION OF THE PREFERRED EMBODIMENT

Figure 1:
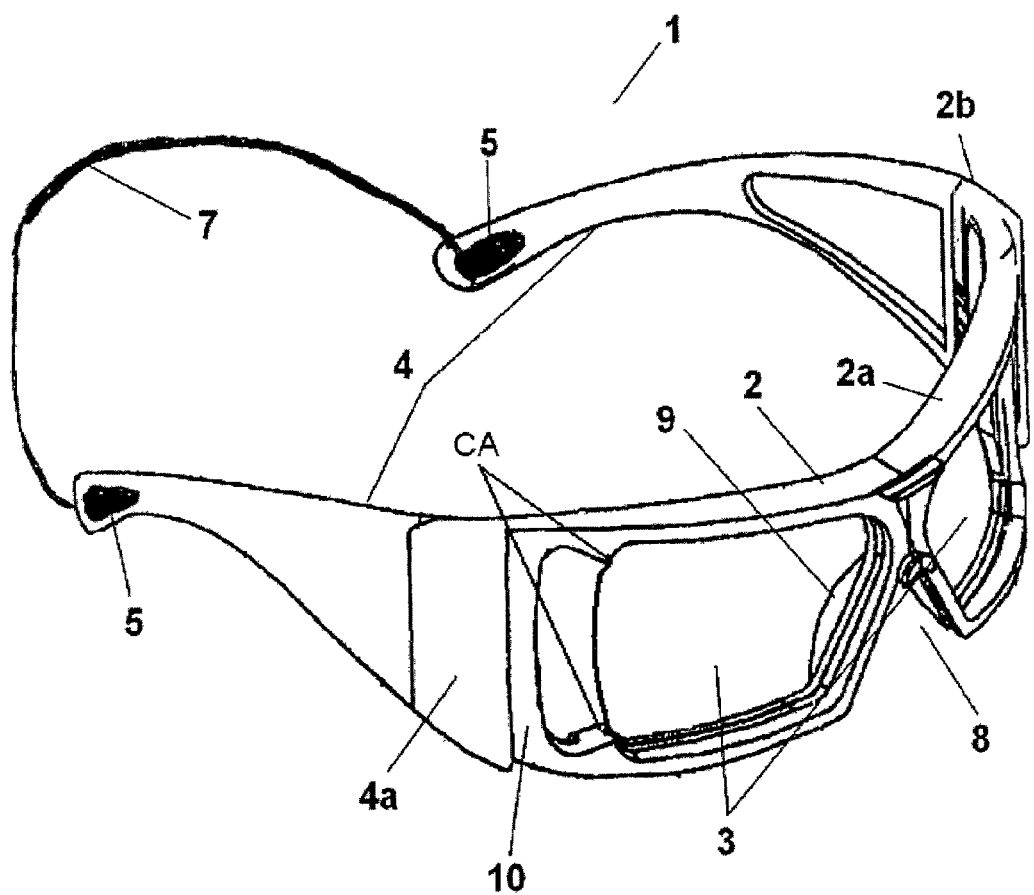
FIG. 1 is a perspective view of the goggles of the instant invention.
Figure 7:
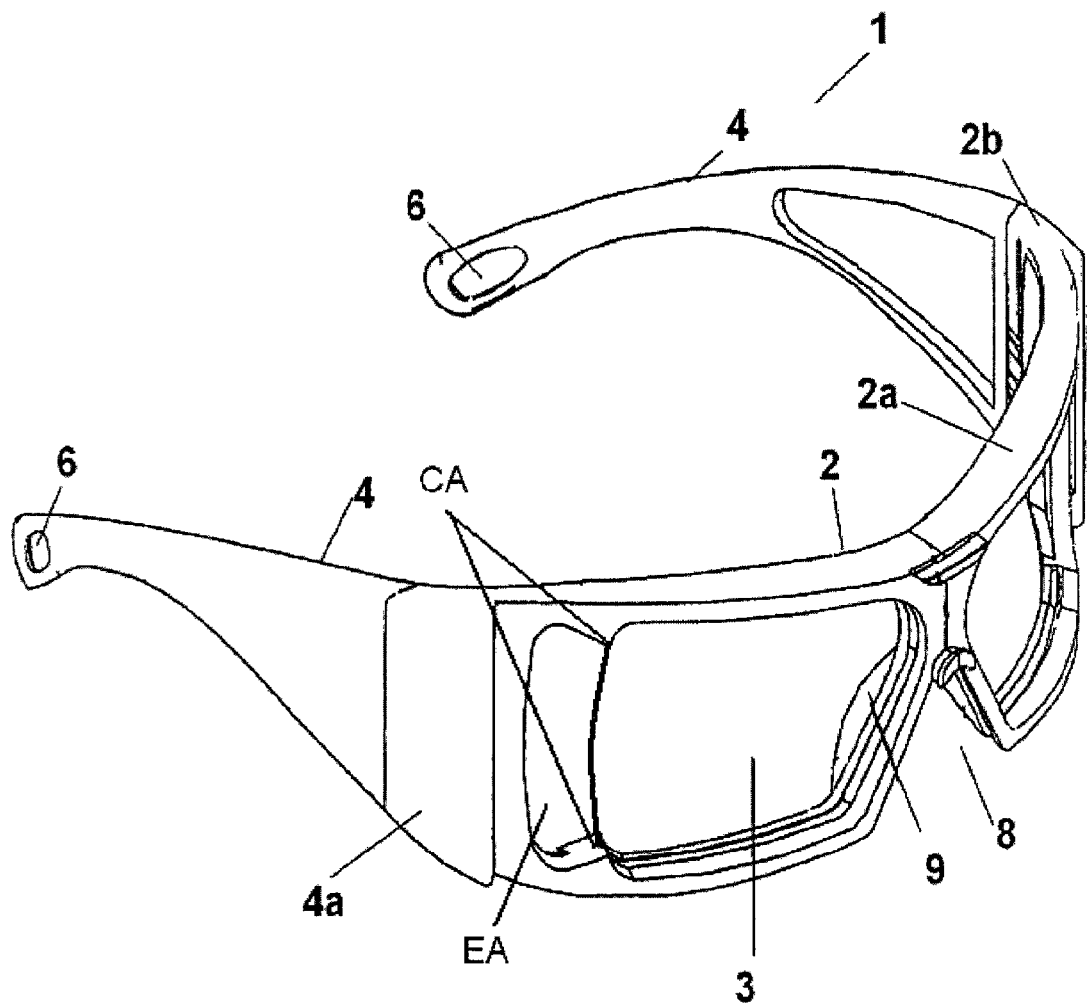
FIG. 7 is another perspective view of the goggles of the instant invention.

With reference to FIGS. 1 and 7, industrial safety goggles 1 are shown, consisting of a frame 2 onto which ophthalmic micas 3 are mounted. The frame includes two sidepieces 4, at which end pads 5 are placed that are press fitted into holes 6 and joined between them by a tape or cord 7. The bridge 8 of the frame 2 can also be seen with an inserted soft and anti-slippage pad 9 offering a convenient engagement on the bridge of the user's nose.

The frame 2 is a complete ring offering better impact resistance and prolonging the useful life of the industrial protection goggles 1.

The pads 5 allow a better adherence of the goggles 1 onto the user's head and the cord 7 permits an easy rupture in case of a sudden tension if the goggles 1 are accidentally blocked by an object, preventing thus an accident.

The frame 2 contains an upper protection 2a and side protections 2b to protect the eyes against projectiles or impacts.

Sidepieces 4 have additional lateral protections 4a as continuation of the front part of the frame 2, fitting because of their extended design, offering thus additional protection.

The frame 2 allows ventilation and prevents the fogging of the ophthalmic micas 3, ensuring a firm assembly and preventing the rotation and/or accidental disassembly of the ophthalmic micas 3 from the frame 2.

Figure 2:
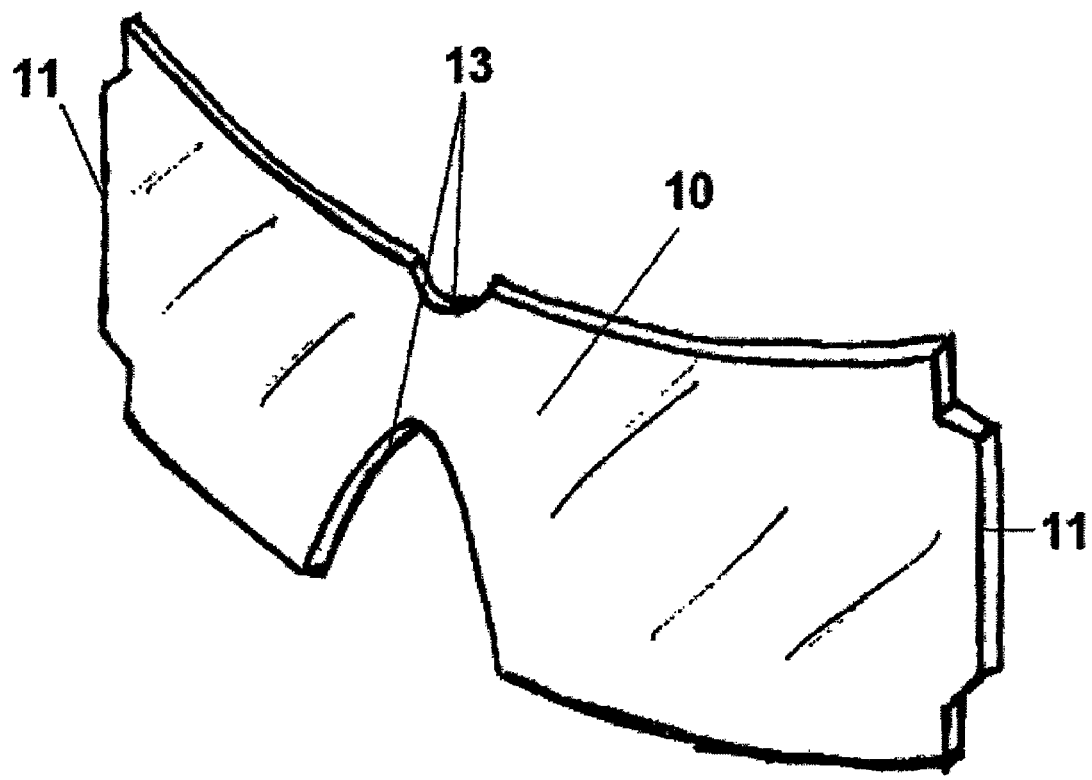
FIG. 2 is a perspective view of the impact protection mica for the goggles of FIG. 1.

The specific characteristics of the impact protection mica 10 are illustrated in FIG. 2 in which the mica includes two side projections 11 that are inserted in the side ends 12 of the frame 2 (FIG. 4a), and recesses 13 to assemble the mica 10 onto the frame 2.

In FIGS. 3a, 3b and 3c, one of the pads 5 is shown in detail, inserted in the end of each sidepiece 4 of the frame 2, in the holes 6 specially made for this purpose. The pads 5 are removable, soft and anti-slippage and offer better convenience in the mastoid area and ensure the non slippage of the frame 2.

Figure 4A:
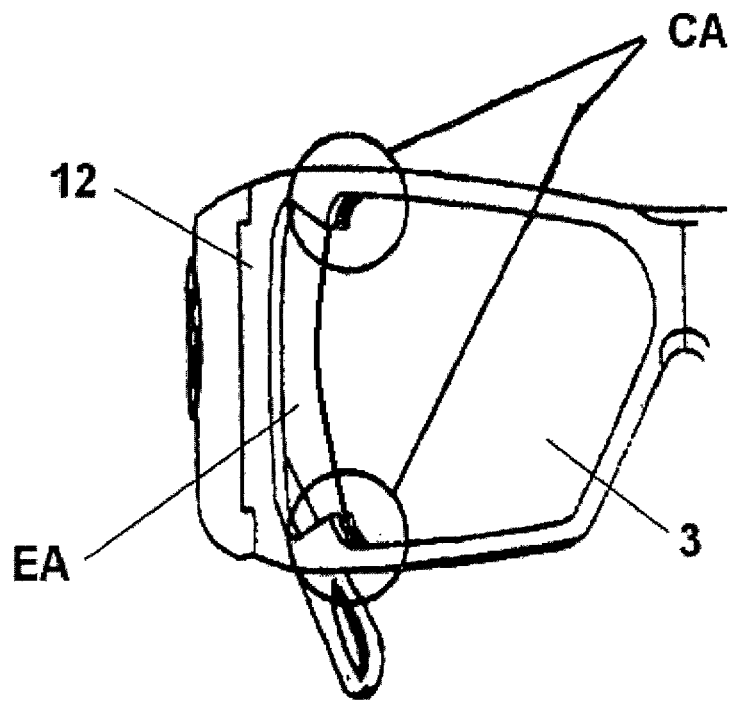
FIG. 4a shows in detail the left part of the frame of the goggles of FIG. 1.
Figure 4B:
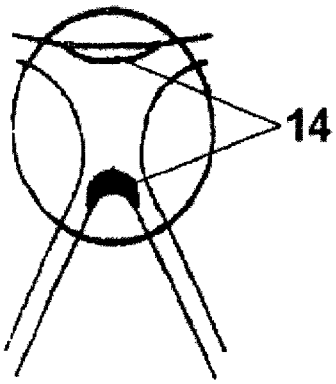
FIG. 4b shows in detail the central part of the frame of the goggles of FIG. 1.
Figure 4C:
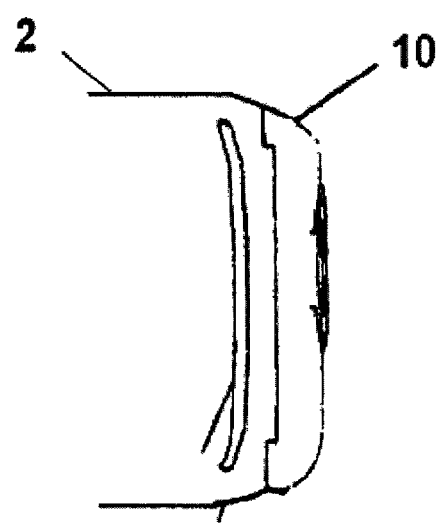
FIG. 4c shows in detail the left side part of the frame of the goggles of FIG. 1.

In FIGS. 4a, 4b and 4c, the attachment system of the ophthalmic micas 3 can be seen, as well as the attachment system of the protection mica 10.

Figure 5:
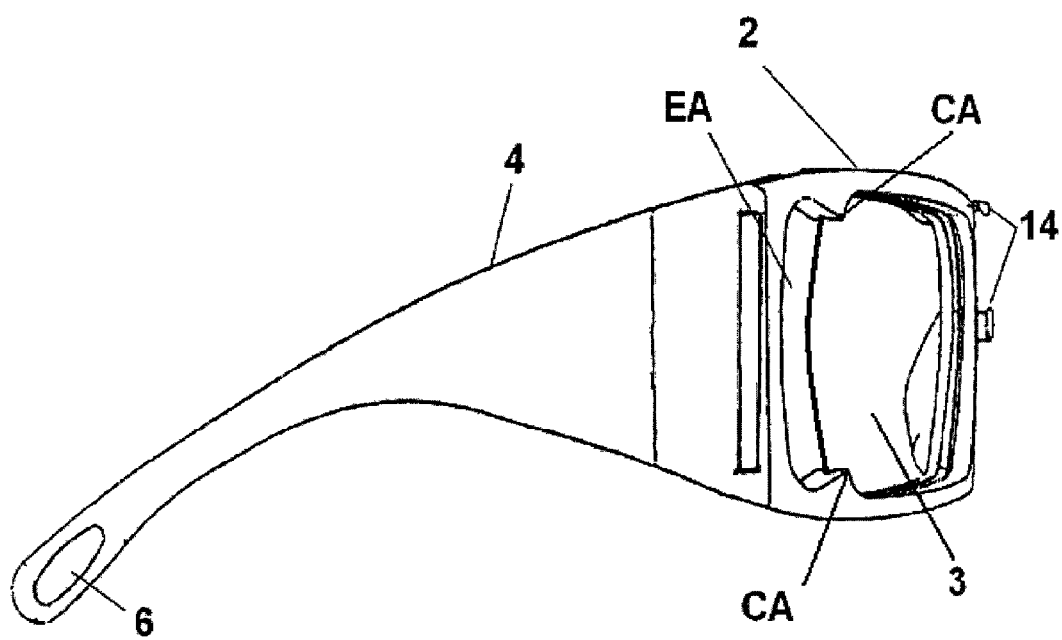
FIG. 5 is a left side view of the goggles of FIG. 1.

From FIGS. 4a and 5, the open space EA permitting the ventilation of the face of the goggle's user 1 can be seen as well as the elements 14 located on the frame 2; said elements 14 are to be inserted in the recesses 13 of the protection mica 10, fastening it onto the frame 2.

The frame 2 has an open space as ventilation part EA (FIG. 4a) in both eyes, between the graduated mica and the end of the ring, preventing the fogging of the ophthalmic mica 3.

Figure 6:
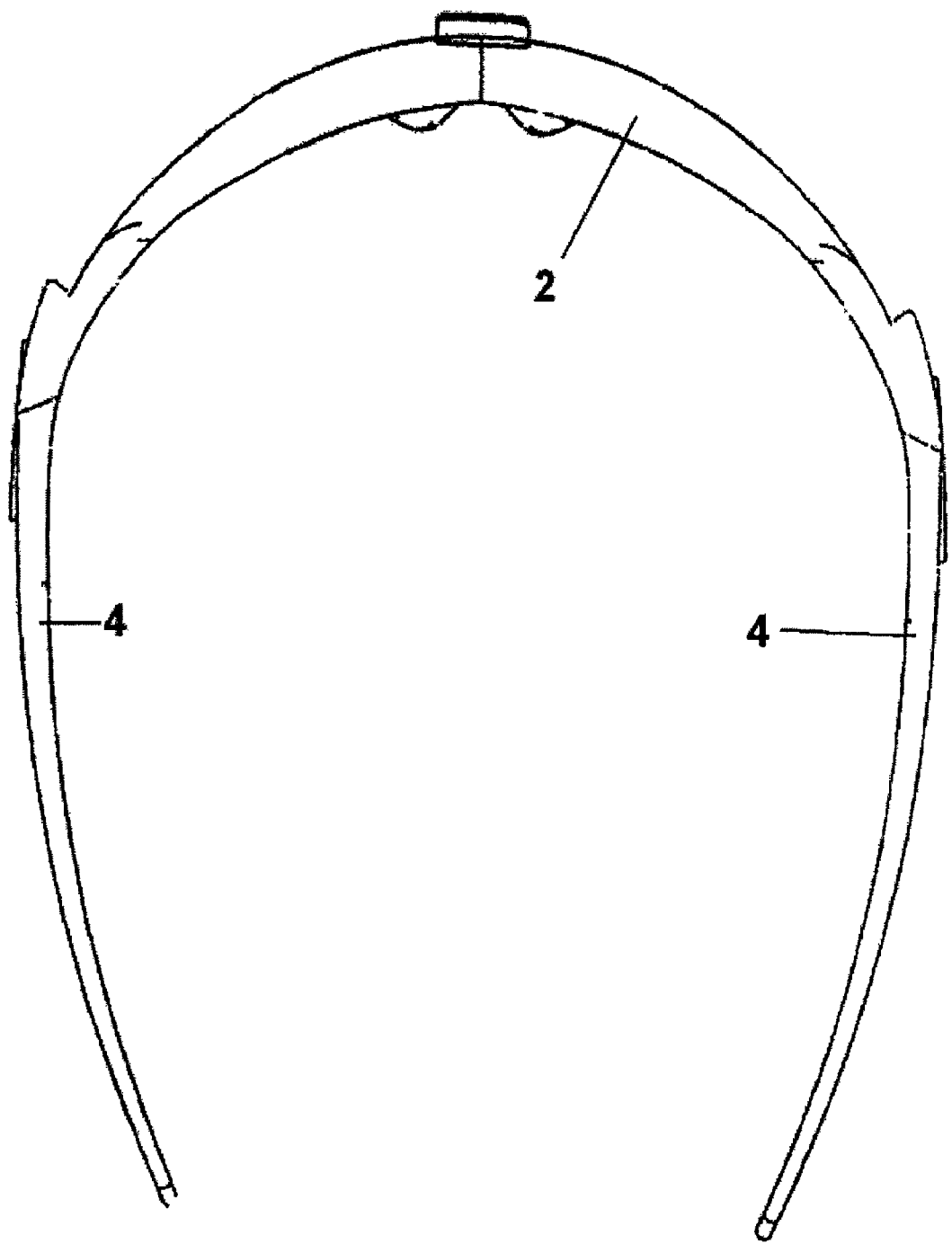
FIG. 6 is an upper view of the goggles of FIG. 1.

From FIG. 6, an upper view of the frame 2 can be seen, specially the curve shape of said frame and of the sidepieces 4 that facilitates the positioning onto the user's head.

Each ring has an upper angular notch and a bottom angular notch CA (FIGS. 4a and 5) permitting the firm fastening of the ophthalmic mica 3. Said notches are a continuation of the bevel serving to mount the ophthalmic mica 3 onto the frame 2 (FIGS. 1 and 7), ensuring a firm assembly and preventing the rotation and/or accidental disassembly of the ophthalmic mica 3 from the frame 2.

The instant invention has been described and illustrated in its preferred embodiment, however, a person ordinarily skill in the art can contemplate variations that are included within the scope of the following claims.

What is claimed is:

1. Protection goggles comprising a frame having two rings, two side ends, a central part of the frame between said rings, a bridge adapted to engage the goggles on a user's nose and two sidepieces; graduated micas mounted on said rings; one single-piece impact protection mica mounted on the frame in front of said graduated micas; said protection mica having side projections inserted in said side ends of said frame; said impact protection mica having recesses in said central part for fitting into the central part of the frame; wherein each said ring has, near said side ends, an upper angular notch and a bottom angular notch for mounting each said graduated mica onto the frame to prevent unintended movement of the graduated micas from said frame; said frame has a ventilation part in each of said rings disposed between said graduated mica and an end of the ring to prevent fogging of the graduated mica.

2. The goggles according to claim 1, wherein said impact protection mica is made of polycarbonate with anti-scratch treatment and protection against ultraviolet rays.

3. The goggles according to claim 1, wherein pads on said sidepieces have a cord integrated to hang around the neck when the goggles are not in use.

4. The goggles according to claim 1, wherein said sidepieces have a curvature complimentary to a skull of a user.

5. The goggles according to claim 1, wherein said sidepieces include removable pads, at their ends, in order to ensure that the frame does not slip.

6. The goggles according to claim 1, wherein said bridge has an anti-slip pad inserted.

7. The goggles according to claim 1, wherein said frame contains an upper protection and side protections to protect the eyes against projectiles.

* * * * *